United States Patent [19]

Noble et al.

[11] Patent Number: 5,062,854

[45] Date of Patent: Nov. 5, 1991

[54] PROSTHETIC DEVICE AND METHOD OF IMPLANTATION

[75] Inventors: Philip C. Noble, Houston, Tex.; Mary B. Padgett, Parsippany, N.J.

[73] Assignee: Pfizer Hospital Products Group, New York, N.Y.

[21] Appl. No.: 557,272

[22] Filed: Jul. 24, 1990

Related U.S. Application Data

[62] Division of Ser. No. 255,206, Oct. 7, 1988, Pat. No. 5,002,560.

[51] Int. Cl.$^5$ .............................................. A61F 2/34
[52] U.S. Cl. ...................................................... 623/23
[58] Field of Search ........................ 623/16, 18, 22, 23, 623/66

[56] References Cited

U.S. PATENT DOCUMENTS

| Re. 31,865 | 4/1985 | Roux | 623/16 |
|---|---|---|---|
| 2,719,522 | 10/1955 | Hudack | 623/18 |
| 3,067,740 | 12/1962 | Haboush | 623/23 |
| 3,793,650 | 2/1974 | Ling et al. | 623/18 |
| 3,820,167 | 6/1974 | Sivash | 623/23 |
| 3,874,003 | 4/1975 | Moser et al. | 623/18 |
| 3,894,297 | 7/1975 | Mittelmeier et al. | 623/23 |
| 3,906,550 | 9/1975 | Rostoker et al. | 623/23 |
| 3,924,275 | 12/1975 | Heimke et al. | 623/22 |
| 3,938,198 | 2/1976 | Kahn et al. | 623/16 |

(List continued on next page.)

FOREIGN PATENT DOCUMENTS

| 0187903 | 7/1986 | European Pat. Off. . | |
|---|---|---|---|
| 2247721 | 4/1974 | Fed. Rep. of Germany . | |
| 2628929 | 1/1977 | Fed. Rep. of Germany | 433/176 |
| 2475892 | 8/1981 | France . | |
| 2549718 | 2/1985 | France . | |
| 2575383 | 7/1986 | France | 623/18 |
| 2600527 | 12/1987 | France | 623/22 |
| 471394 | 5/1952 | Italy | 623/23 |
| WO88/01854 | 3/1988 | PCT Int'l Appl. | 623/18 |
| WO89/08436 | 9/1989 | PCT Int'l Appl. . | |
| 1409053 | 10/1975 | United Kingdom . | |
| 2162065 | 1/1986 | United Kingdom | 623/18 |

OTHER PUBLICATIONS

Whiteside Total Hip System, Dow Corning Wright, Nov., 1985.
Osteonics Technical Bulletin, Issue: Thigh Pain, 1988.
Whiteside et al., The Effects of Collar on Total Hip Femoral Component Subsidence, 231, Clinical Orthopedics and Related Research, 120 (Jun. 1988).

*Primary Examiner*—David J. Isabella
*Attorney, Agent, or Firm*—Pennie & Edmonds

[57] ABSTRACT

The bone prosthesis of the present invention comprises a first body member or stem for placement into a bone cavity, such as an intramedullary canal. The body member is configured and dimensioned so as to provide a nonuniform interference press-fit. The apparatus further comprises a second body member or broach for placement into and removal from a bone cavity, the broach configured and dimensioned so as to prepare the bone cavity so as to provide a nonuniform interference press-fit with the stem. The apparatus further comprises a distal sleeve configured and dimensioned so as to be attached to the stem so as to centralize the stem in the bone cavity. The distal sleeve preferably is provided with an interior conical slope and an exterior conical slope on a portion thereof to aid in insertion into the canal. The stem further comprises at least one groove and preferably a plurality of grooves along its corners. These grooves are nonparallel to the longitudinal axis of the stem and do not extend over any one entire side of the stem. The stem can be provided with an area of concellous texture which comprises substantially randomly patterned array of multiple curved-line surface unevenness, such as indentations or protrusions. The present invention also is directed to a method comprising utilization of the broach, the stem and the distal sleeve so as to provide a nonuniform press-fit between the bone prosthesis and the bone cavity while centralizing the stem in the bone cavity.

7 Claims, 4 Drawing Sheets

U.S. PATENT DOCUMENTS

| | | | |
|---|---|---|---|
| 3,943,576 | 3/1976 | Sivash | 623/23 |
| 3,977,026 | 8/1976 | Battault | 623/16 |
| 3,987,499 | 10/1976 | Scharbach et al. | 623/18 |
| 3,996,625 | 12/1976 | Noiles | 623/18 |
| 4,065,817 | 1/1987 | Branemark et al. | 623/16 |
| 4,184,213 | 1/1980 | Heimke | 623/18 |
| 4,187,559 | 2/1980 | Grell et al. | 623/18 |
| 4,199,824 | 4/1980 | Niederer | 623/23 |
| 4,231,120 | 11/1980 | Day | 623/18 |
| 4,262,369 | 4/1981 | Roux | 623/22 |
| 4,268,920 | 5/1981 | Engelbrecht | 623/18 |
| 4,272,855 | 6/1981 | Frey | 623/18 |
| 4,292,695 | 10/1981 | Koeneman | 623/18 |
| 4,314,381 | 2/1982 | Koeneman | 623/23 |
| 4,385,405 | 5/1983 | Teinturier | 623/23 |
| 4,404,692 | 9/1983 | Eftekhar | 623/18 |
| 4,406,023 | 9/1983 | Harris | 623/18 |
| 4,430,761 | 2/1984 | Niederer et al. | 623/23 |
| 4,450,592 | 5/1984 | Niederer et al. | 623/23 |
| 4,459,708 | 7/1984 | Buttazzoni | 3/1.91 |
| 4,519,101 | 5/1985 | Schreiber et al. | 623/23 |
| 4,523,587 | 6/1985 | Frey | 623/18 |
| 4,535,487 | 8/1985 | Esper et al. | 623/18 |
| 4,536,894 | 8/1985 | Galante et al. | 623/23 |
| 4,538,305 | 9/1985 | Engelbrecht et al. | 623/18 |
| 4,546,501 | 10/1985 | Gustilo et al. | 623/23 |
| 4,549,319 | 10/1985 | Meyer | 623/23 |
| 4,595,393 | 6/1986 | Anapliotis et al. | 623/18 |
| 4,608,052 | 8/1986 | Van Kampen et al. | 623/18 |
| 4,619,659 | 10/1985 | Witzel | 623/23 |
| 4,623,349 | 11/1986 | Lord | 623/18 |
| 4,636,219 | 1/1987 | Pratt et al. | 623/18 |
| 4,642,124 | 2/1987 | Cooke | 623/18 |
| 4,645,506 | 2/1987 | Link | 623/23 |
| 4,659,331 | 4/1987 | Matthews et al. | 623/18 |
| 4,661,112 | 4/1987 | Muller | 623/18 |
| 4,666,449 | 5/1987 | Frey et al. | 623/23 |
| 4,670,015 | 6/1987 | Freeman | 623/23 |
| 4,673,409 | 6/1987 | Van Kampen et al. | 623/18 |
| 4,681,589 | 7/1987 | Tronzo | 623/18 |
| 4,685,923 | 8/1987 | Mathys | 623/16 |
| 4,704,686 | 11/1987 | Aldinger | 623/18 |
| 4,715,859 | 12/1987 | Schelhas et al. | 623/18 |
| 4,718,912 | 1/1988 | Crowninshield | 623/18 |
| 4,718,916 | 1/1988 | Morscher | 623/18 |
| 4,728,334 | 3/1988 | Spotorno | 623/18 |
| 4,731,088 | 3/1988 | Collier | 623/18 |
| 4,753,657 | 6/1988 | Lee et al. | 623/18 |
| 4,770,660 | 9/1988 | Averill | 623/18 |
| 4,865,608 | 11/1987 | Brooker et al. | 623/23 |
| 4,878,919 | 11/1989 | Pavlansky et al. | 623/23 |
| 4,888,023 | 12/1989 | Averill et al. | 623/23 |

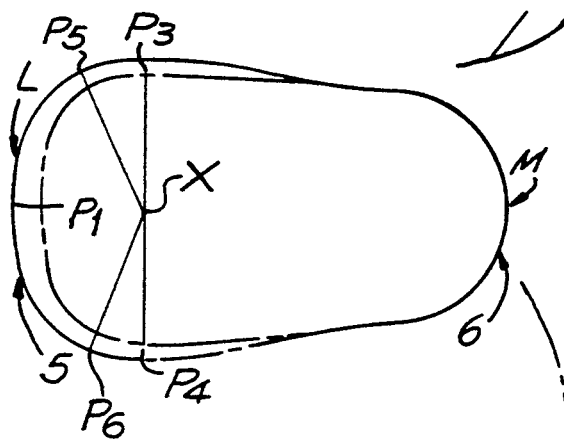
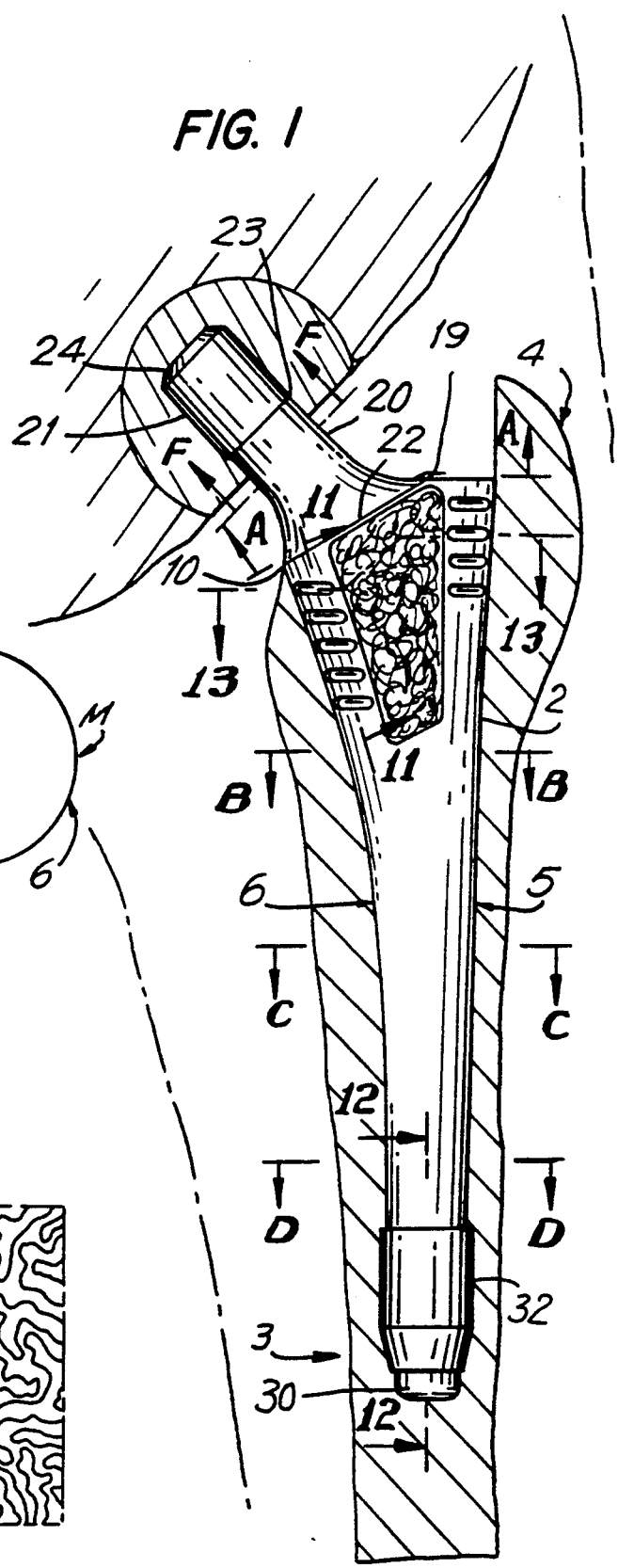
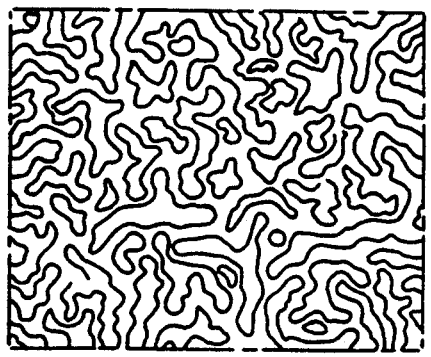

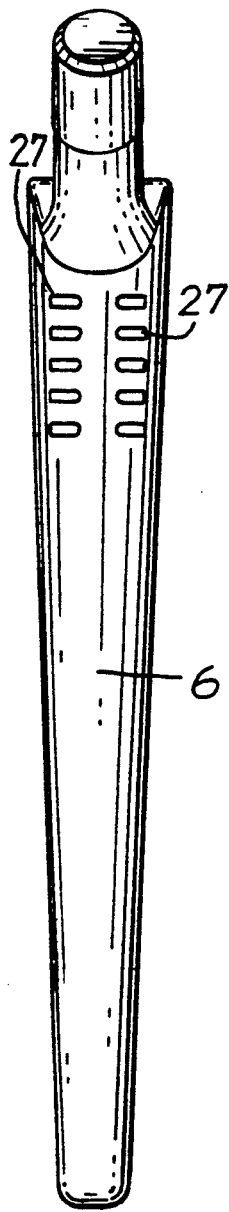
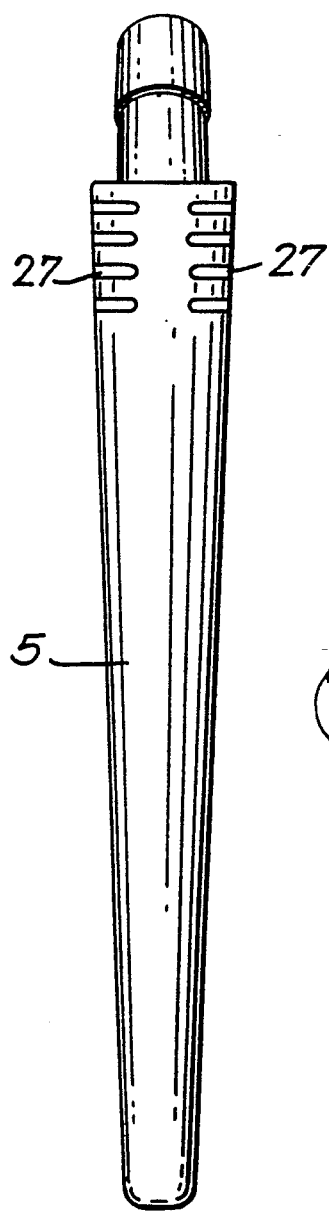
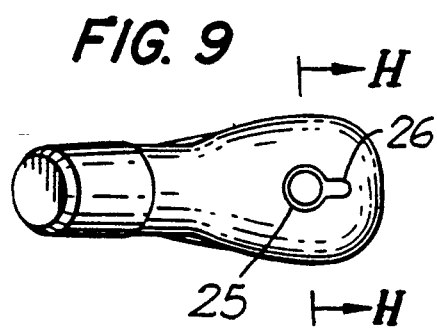
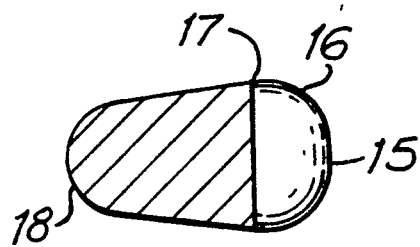
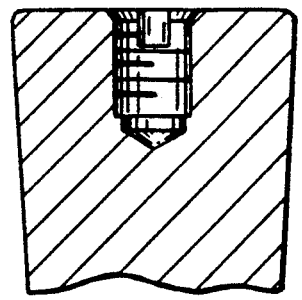

PROSTHETIC DEVICE AND METHOD OF IMPLANTATION this is a division, of application Ser. No. 07/255,206, filed Oct. 7, 1988 now U.S. Pat. No. 5,002,580.

TECHNICAL FIELD

The present invention generally relates to prostheses and in particular to a bone implant which is implanted in a press-fit manner.

BACKGROUND OF THE INVENTION

Acute arthritis or trauma may necessitate the replacement of natural bones and joints with prosthetic devices. For example, the replacement of the hip joint is one of the more common operations performed for these reasons. Such procedures have become somewhat commonplace in the treatment of acute arthritis or trauma not only in human beings but also in animals such as dogs and cats.

With respect to implantation of a hip prosthesis, rigid fixation of femoral components is desirable to promote long term stabilization and also to minimize the occurrence of adverse symptoms after surgery, such as pain and limp. Such fixation is also desirable to minimize bone-implant micromotion.

One known method of prosthesis fixation involves the use of cement. However, in time cement can loosen with undesired results. Such results and other undesirable effects from cement use are described in U.S. Pat. No. 4,406,023.

In an attempt to achieve such rigid fixation but without cement, hip prostheses have been inserted into bone canals to obtain a press-fit arrangement. A review of known hip implants is presented in Noble et al., "The Myth of 'Press-Fit' in the Proximal Femur," America Academy of Orthopedic Surgeons 55th Annual Meeting, Atlanta, Ga., Feb. 4–9, 1988, which is incorporated herein in its entirety by reference.

However, some of the shortcomings of these hip implants include that they are stabilized by contact with cortical bone in separate regions of the medullary canal and that the interfaces do not constitute a press-fit.

Secondly, rigid fixation is also dependent on the surface texture of the hip implant which is press-fit into the medullary canal. A typical finish in known devices includes a satin or sand-blasted finish. But this surface is not acceptable if implant micromotion is to be minimized. A fuller discussion of surface texture is set forth in E. Kamaric, P. C. Noble and J. W. Alexander, "The Effect of Proximal Surface Texture on the Acute Stability of Cementless Fixation", a copy of which is submitted herewith and incorporated in its entirety.

We have invented an improved bone prosthesis which overcomes the aforementioned problems and provides for more rigid fixation within the intramedullary canal of a bone.

SUMMARY OF THE INVENTION

The present invention is directed to a prosthetic implant which achieves improved endosteal contact, and reduces the occurrence of gaps at the bone/implant interface. The prosthetic implant of the present invention minimizes implant micromotion.

The present invention comprises an apparatus which comprises a body member for placement into a bone cavity, the body member configured and dimensioned so as to provide a nonuniform interference press-fit within the bone cavity along a portion of the proximal end surface of the body member.

The bone cavity into which the apparatus of the present invention is placed may be an intramedullary canal of a bone.

The apparatus of the present invention may be provided with at least one groove on a portion of said body member, and said grooves may extend over less than the circumference of the body member.

The apparatus of the present invention may be provided with surface unevenness on a portion of the body member.

The present invention comprises a first body member and a second body member, the first body member for insertion into and removal from a bone cavity, the second body member for placement into said bone cavity, the first body member configured and dimensioned so as to prepare the bone cavity so as to provide a nonuniform interference press-fit with the second body member, and the second body member configured and dimensioned so as to provide a nonuniform interference press-fit with the body cavity after the first body member is removed therefrom. The present invention may further comprise such an apparatus wherein the nonuniform interference press-fit comprises an interference press-fit between a portion of the second body member and a portion of the sides of said bone cavity which possess a substantial layer of cancellous bone. The present invention may further comprise such an apparatus wherein the nonuniform interference press-fit further comprises a substantially line-to-line fit between a portion of the second body member and a portion of the side or sides of the bone cavity which do not possess a substantial layer of cancellous bone but rather possess a substantial layer of cortical bone. The present invention further comprises an apparatus wherein the second body member defines a longitudinal axis and a circumference, the body member having an anterior side, a posterior side, a lateral side and a medial side, the second body member being provided with at least one groove along each of the antero-lateral, postero-lateral, antero-medial and postero-medial edges, each of the grooves extending in a plane not parallel to the longitudinal axis of the body member, each of the grooves extending over less than an entire side of the anterior side, posterior side, lateral side and medial side, the second body member further being provided with a cancellous texture on a portion thereof. The present invention may further comprise such an apparatus further comprising a third body member, the third body member configured and dimensioned so as to be attached to the second body member, the third body member configured and dimensioned so as to centralize the second body member in the bone cavity, the third body member being substantially cylindrical and hollow, the third body member defining a longitudinal axis and having a first end and a second end, the third body member being provided with an interior conical slope so as to narrow the inside diameter at the second end as compared to the first end, and the third body member being provided with an external conical slope on a portion thereof so as to narrow the outside diameter thereof at the second end as compared to the first end.

The present invention further comprises a method comprising inserting and removing a first body member into a bone cavity, the first body member configured and dimensioned so as to prepare the bone cavity so as to provide a nonuniform interference press-fit with a second body member, and placing the second body member into the bone cavity, the second body member configured and dimensioned so as to form a nonuniform interference press-fit with the bone cavity.

The present invention further comprises such a method wherein the nonuniform interference press-fit comprises an interference press-fit between a portion of the second body member and a portion of the side or sides of said bone cavity which possess a substantial layer of cancellous bone. The present invention may further comprise such a method wherein the nonuniform interference press-fit further comprises a substantially line-to-line fit between a portion of the second body member and a portion of the side or sides of the bone cavity which do not possess a substantial layer of cancellous bone but rather possess a substantial layer of cortical bone. The present invention further comprises such an apparatus wherein the second body member defines a longitudinal axis and a circumference, the body member having an anterior side, a posterior side, a lateral side and a medial side, the second body member being provided with at least one groove along each of the antero-lateral, postero-lateral, antero-medial and postero-medial edges, each of the grooves extending in a plane not parallel to the longitudinal axis of the body member, each of the grooves extending over less than an entire side of the anterior side, posterior side, lateral side and medial side, the second body member further being provided with a cancellous texture on a portion thereof. The present invention further comprises an apparatus further comprising a third body member, the third body member configured and dimensioned so as to be attached to the second body member, the third body member configured and dimensioned so as to centralize the second body member in the bone cavity, the third body member being substantially cylindrical and hollow, the third body member defining a longitudinal axis and having a first end and a second end, the third body member being provided with an interior conical slope so as to narrow the inside diameter at the second end as compared to the first end, and the third body member being provided with an external conical slope on a portion thereof so as to narrow the outside diameter thereof at the second end as compared to the first end.

The present invention further comprises providing the prosthesis with a body member designed such that at least a portion of the side or sides of the bone cavity into which the device is implanted which possess a relatively substantial layer of cancellous bone will form an interference press-fit with a portion of the body member of the prosthesis, at which time the bone cavity may be prepared or broached forming an envelope. Further, the body member of the device is designed such that the side or sides of the bone cavity into which the device is implanted which do not possess a relatively substantial layer of cancellous bone, but rather possess a surface layer substantially comprised of cortical bone, will not interfere with the insertion of the body member but will maintain a substantially line-to-line fit with a portion of the body member. Design of the prosthetic device in this manner thereby allows a press-fit implantation in which the device forms an interference press-fit with the envelope of the bone cavity on those sides of the envelope which are substantially cancellous bone, and in which the device does not encounter interference but rather forms a substantially line-to-line fit on those sides of the envelope which are substantially cortical bone. A broach may be provided which is also designed in accordance with the present invention, which broach may be inserted into the bone cavity prior to the insertion of the stem to assure a proper fit of the stem therein.

The present invention further comprises a method which comprises preparing a bone cavity for placement of a body member therein so as to provide an interference press-fit along a predetermined portion of said body member. The method comprising preparation of the bone cavity may comprise preparing the bone cavity for placement of the body member therein so that at least a portion of the portions of the bone cavity which posses a relatively substantial layer of cancellous bone will form an interference press-fit with a portion of the bone cavity which does not possess a surface layer comprised substantially of cortical bone, but rather possesses a layer substantially comprised of cortical bone will not interfere with the body member but will maintain a line-to-line fit with a portion of the body member. The method of the present invention comprises insertion and removal of a broach into the bone cavity prior to placement of the body member therein. The broach is configured and dimensioned so as to provide the bone cavity with an envelope configured and dimensioned in accordance with the method of preparing a bone cavity described above in this paragraph.

In accordance with the method of the present invention, if the bone cavity is the intramedullary canal of a human femur, a portion of at least one of the lateral, anterior and posterior sides of the bone cavity will be prepared so as to provide an interference press-fit and a portion of at least one of the medial, anterior and posterior sides of the bone cavity will be prepared so as to provide a substantially line-to-line fit with a portion of the body member.

The present invention comprises providing the prosthesis with at least one groove, the grooves extending in a plane not parallel to the longitudinal axis of the body member, the grooves preferably uniformly spaced along at least one of the antero-lateral, postero-lateral, antero-medial and postero-medial edges of the prosthesis. It is further preferred that the grooves extend only on the edges of the device, and do not completely extend over the sides of the body member. The present invention further comprises providing a portion of the body member and preferably at least one of the anterior or posterior sides of the body member of the prosthesis with a substantially randomly patterned array of multiple curved-line surface unevenness, such as indentations or protrusions, defining a cancellous texture. Both the above-defined horizontal grooves and the cancellous texture are preferably obtained by forging or casting the prosthetic device, however any suitable process may be employed.

The present invention further comprises body member configured and dimensioned so as to be placed in a bone cavity, the body member comprising at least one groove of a predetermined length.

The present invention further comprises an apparatus comprising a body member for placement into a bone cavity, the body member defining a circumference, the body member comprising a macro texture on a portion thereof. The present invention further comprises such an apparatus further comprising the body member comprising an anterior side, a posterior side, a lateral side and a medial side, the body member comprising the macro texture at least on one of the antero-lateral, postero-lateral, antero-medial and postero-medial edges. The present invention further comprises such an apparatus further comprising the body member comprising the macro texture on at least each of said antero-lateral, antero-medial, postero-lateral and postero-medial edges, and also further comprises such an apparatus further comprising the macro texture being provided only on each of the antero-lateral, antero-medial, postero-lateral and postero-medial edges of the body member.

The present invention is further directed to an apparatus comprising a body member configured and dimensioned so as to be attached to a second apparatus, such as a bone prosthesis, which is configured and dimensioned so as to be placed in a bone cavity, the body member configured and dimensioned so as to centralize the second apparatus in the bone cavity, which bone cavity may be an intramedullary canal of a bone. The body member may be configured and designed so as to be 1 millimeter smaller or less than 1 millimeter smaller in diameter then the intramedullary canal of the bone at the point in the intramedullary canal where the body member is placed. The body member is preferably sized so as to be identical in diameter to the intramedullary canal of the bone at the point where the body member is placed, however, it has been found that if the body member is not more than 0.5 mm smaller, and preferably not more than 0.25 mm smaller, in diameter a most satisfactory stabilization of the bone prosthesis is achieved. Further, the body member may be substantially cylindrical and hollow, the body member defining a longitudinal axis and having a first end and a second end, the body member being provided with an interior conical slope in the longitudinal direction on a portion thereof so as to narrow the inside diameter at the second end as compared to the first end, and the body member being provided with an external conical slope on a portion thereof so as to narrow the outside diameter at the second end as compared to the first end.

DESCRIPTION OF THE DRAWINGS

The present invention is described in detail below with reference to the drawings wherein:

FIG. 1 is a frontal view of a hip prosthesis according to the present invention as shown implanted in the medullary canal of a human femur.

FIG. 2 is a lateral view of the hip prosthesis of FIG. 1.

FIG. 3 is a medial view of the hip prosthesis of FIG. 1.

FIG. 7 is a cross-sectional view taken along line A—A of FIG. 1.

FIG. 9 is a top view of the hip prosthesis of FIG. 1 illustrating an implantation slot or threaded cavity.

FIG. 10 is a cross-sectional view taken along line H—H of FIG. 9.

FIG. 14 is a top view of the contour of the medullary canal in comparison to the corresponding larger area of the hip prosthesis to illustrate the press-fit of the hip prosthesis according to the present invention.

FIG. 15 is an enlarged view of the uneven surface of the hip implant of FIG. 1.

DETAILED DESCRIPTION OF THE PREFERRED EMBODIMENT

Figure 13:
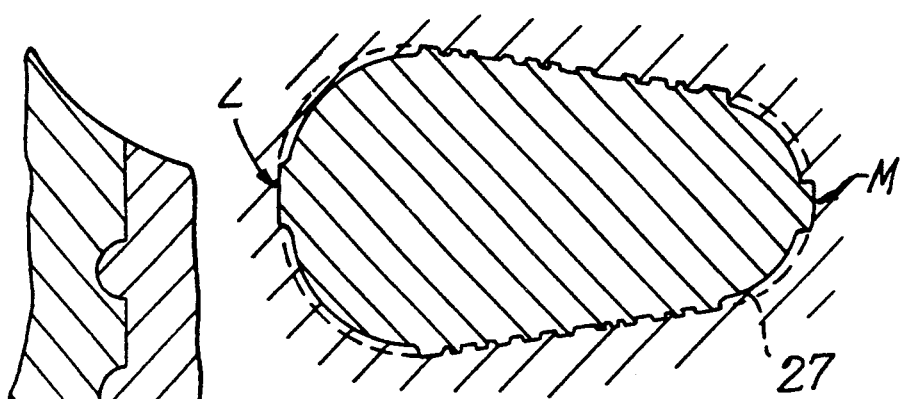
FIG. 13 is a cross-sectional view taken along line 13—13 of FIG. 1.
Figure 11:
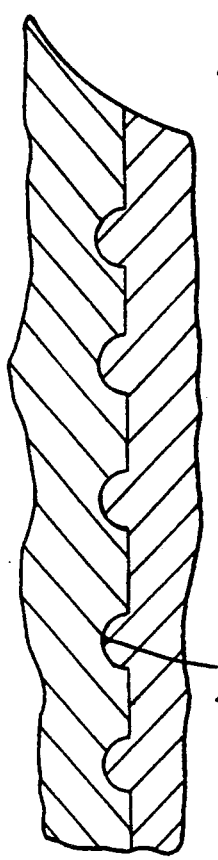
FIG. 11 is a cross-sectional view taken along 11—11 of FIG. 1.

In the description which follows, any reference to either orientation or direction is intended primarily for the purpose of illustration and is not intended in any way as a limitation of the scope of the present invention.

While it is presently contemplated that the preferred embodiment of the present invention is a hip implant, as will be described herein, the present invention is not limited to use as a hip implant but may be used as a prosthetic implant of any type. While it is also presently contemplated that the preferred embodiment of the present invention is particularly well suited for press-fit implantation, the present invention is not limited to press-fit implantation, but embodies implantation in any manner. Further, the dimensions recited herein are typical of one of the many various sizes of hip implants embodying the present invention and are not intended to limit the invention.

The apparatus of the present invention may be provided with surface unevenness on a portion of the body member. The surface unevenness may comprise a substantially randomly patterned array of multiple curved-line surface unevenness, such as indentations or protrusions, defining a cancellous texture, and as used herein the term "cancellous texture" will define such a surface unevenness. The surface unevenness and the grooves may both be provided on the body member, but the present invention is not limited thereto. The cancellous texture can be a macro texture.

As used herein, an "interference press-fit" is defined as a mechanical connection formed by two components, at least one of which is deformable, where the adjacent boundary lines of the two components overlap and interfere with each other such that the two components must be forced into a position adjacent each other whereupon the deformation of one component causes a reaction force to be developed over the area of contact between the two components. As used herein, a "line-to-line fit" is defined as a mechanical connection formed by two components where the adjacent boundary lines of the two components match each other evenly without any overlap or interference. As used herein, the term "press-fit" is a mechanical connection formed by the substantial matching of two components and encompasses both an interference press-fit and a line-to-line fit. The term "nonuniform interference press-fit" herein defines a press-fit comprising both an interference press-fit and a line-to-line fit wherein the interference press-fit comprises a varying amount of overlapping and interference.

As used herein, when defining a texture, the term "macro" defines a roughness, such as indentations or protrusions, comprising various features which are 1 mm or greater in depth or height and which are spaced from one another by a distance of 1 mm or greater. A macro texture in accordance with the present invention can include features ranging from 1 to 5 mm in depth or height and spaced from one another by a distance ranging from 1 to 5 mm. As used herein, the term "predetermined length" includes a partial or entire circumference of a body member and the longitudinal length of a body member. A predetermined length can extend in any direction. As used herein, the term "proximal" refers to the portion of the prosthesis positioned closest the entrance of the bone cavity, and the term "distal" refers to the portion of the prosthesis positioned farthest within the bone cavity.

Figure 4:
FIG. 4 is a cross-sectional view taken along line D—D of FIG. 1, with the distal sleeve removed therefrom.
Figure 16:
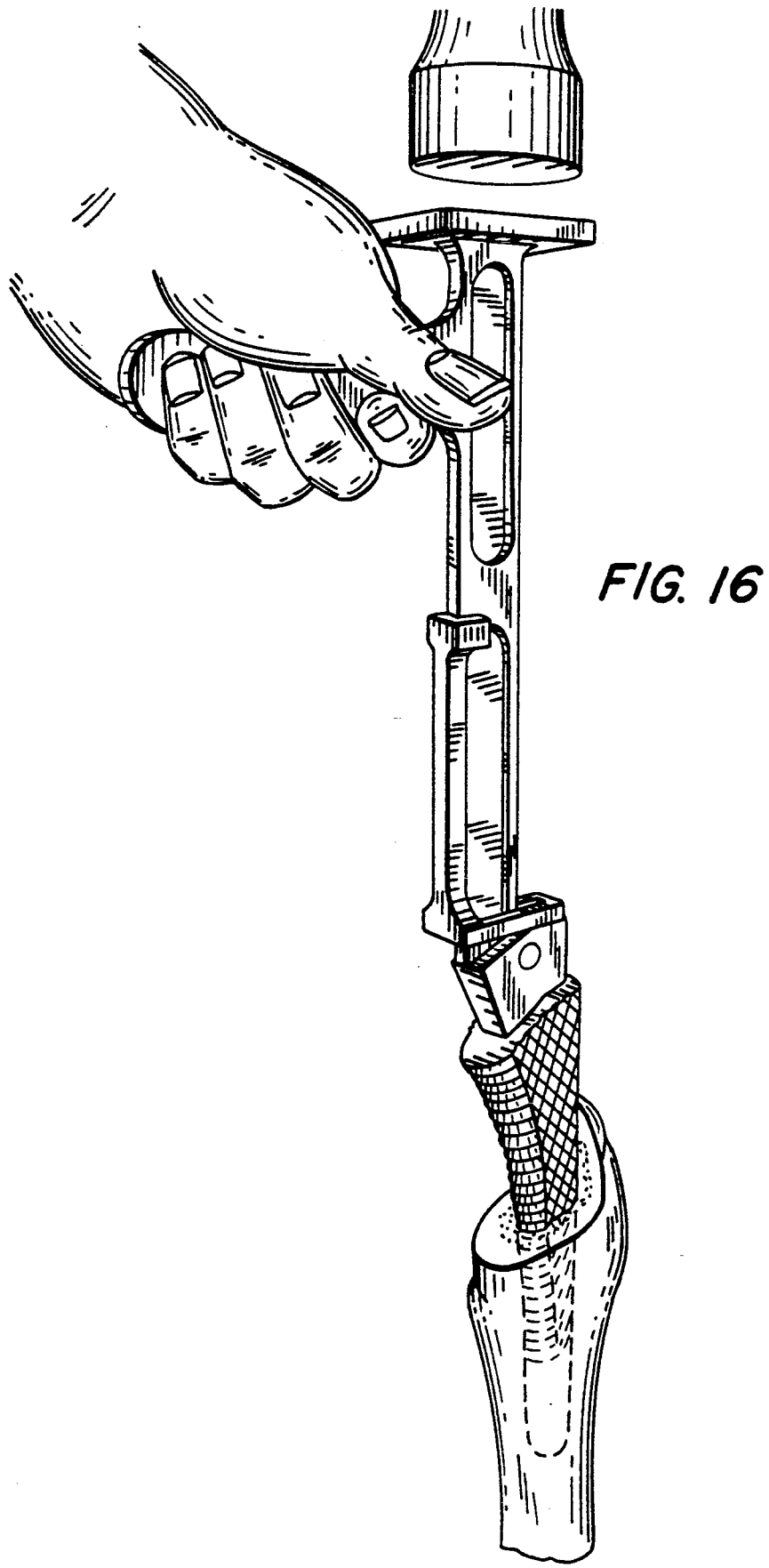
FIG. 16 is an illustration of the method of preparing a bone canal utilizing a broach according to the present invention.

As used herein, the term "central axis" defines a line defined by the center points of two cross sections of the body member at the distal end, such as center point $CP_1$ of FIG. 4 and a center point of a cross section of the body member adjacent the cross section of FIG. 4, and extends in a proximal-distal direction through the entire body member. Referring to FIG. 14, point X is the point on the proximal end of the body member at which the central axis terminates. Referring to FIG. 14, point $P_1$ is a point on the lateral side of the proximal end of the body member from which an isosceles triangle can be formed by drawing two lines, R and S, each which terminate at a point equidistant from point X and drawing a third line, RXS, connecting the terminating points of R and S with a line which intersects X. As used herein, the term "centerline" will define a line which extends the width of the proximal end of the body member and includes line RXS as a segment thereof.

The maximum interference is achieved along the lateral edge of the proximal end of the implant, and more particularly at point $P_1$ thereon, as shown in FIG. 14. At $P_1$ the amount of interference ranges from 1 to 3 mm, preferably 1 to 2 mm. The term "percent interference" at any given point Z on the circumference of the body member is defined as the amount of interference, measured in length, at Z divided by the distance from X to a point Q on a line drawn from X to Z defined by the point at which the side of the bone cavity terminated prior to insertion of the body member. At $P_1$, the percent interference ranges from 11 to 30 percent and preferably 11 to 20 percent.

Predetermined amounts of interference are also provided at points $P_3$, which is the termination point of the centerline at its posterior end, and $P_4$, which is the termination point of the centerline at its anterior end. At $P_3$ and $P_4$, the amounts of interference ranges from 1 to 2 mm and preferably 1 to 1.5 mm, and the percent interference ranges from 11 to 18.7 percent and preferably 11 to 14 percent. Furthermore, the amount of interference at $P_3$ and $P_4$ is preferably less than the amount of interference at $P_1$ for a given body member in a given bone cavity.

Further predetermined amounts of interference are also provided at points $P_5$, which is the termination point of a line drawn through X to the posterior side of the body member and 30 degrees to the lateral side of the centerline, and $P_6$, which is the termination point of a line drawn through X to the anterior side of the body member and 30 degrees to the lateral side of the centerline. At $P_5$ and $P_6$, the amount of interference ranges from $\frac{3}{4}$ to 1.5 mm, and preferably $\frac{3}{4}$ to 1 mm, and the percent interference ranges from 7.5 to 13.8 percent and preferably 7.5 to 9.2 percent. Furthermore, the amount of interference at $P_5$ and $P_6$ is preferably less than the amount of interference at $P_3$ and $P_4$ for a given body member in a given bone cavity.

The present invention further comprises a body member for placement in a femur, the body member configured and dimensioned so as to provide a nonuniform press-fit with the femur intramedullary canal, the body member defining a circumference, a centerline and a central axis, the interference press-fit comprising an interference press-fit at $P_1$ comprising an amount of interference equal to the maximum amount present between the body member and the sides of the bone cavity, a predetermined amount of interference at $P_3$ and $P_4$ which is less than the maximum amount, and a predetermined amount of interference occurring at $P_5$ and $P_6$ which is less than the amount occurring at $P_3$ and $P_4$.

The apparatus according to the present invention comprises the maximum amount of interference comprising 1 to 3 millimeters of interference, preferably 1 to 2 millimeters, the amount of interference at $P_3$ and $P_4$ comprising 1 to 2 millimeters of interference, preferably 1 to 1.5 millimeters, the amount of interference at $P_5$ and $P_6$ comprising $\frac{3}{4}$ to 1.5 millimeters of interference, preferably $\frac{3}{4}$ to 1 millimeter, the maximum amount of interference comprising 11 to 30 percent interference, preferably 11 to 20 percent, the amount of interference at $P_3$ and $P_4$ comprising 11 to 18.7 percent interference, preferably 11 to 14 percent, and the amount of interference comprising 7.5 to 13.8 percent interference, preferably 7.5 to 9.2 percent.

The present invention further comprises such an apparatus further comprising a broach, the broach configured and dimensioned so as to be inserted into and removed from the bone canal so as to prepare the bone canal so as to provide the appropriate interference press-fit with the body member.

The present invention further comprises a method comprising inserting and removing a first body member into a bone cavity, the first body member configured and dimensioned so as to prepare the bone cavity so as to provide a nonuniform interference press-fit with a second body member, and placing the second body member into the bone cavity, the second body member configured and dimensioned so as to form a nonuniform interference press-fit with the bone cavity, the bone cavity being an intramedullary canal of a femur, the method further comprising the second body member having an anterior side, a posterior side, a lateral side and medial side, the second body member defining a circumference, a centerline and a central axis, the bone cavity comprising an intramedullary canal of a femur, the nonuniform press-fit comprising an interference press-fit at $P_1$ comprising an amount of interference equal to the maximum amount present between the second body member and the bone cavity, a predetermined amount of interference at $P_3$ and $P_4$ which is less than the maximum amount, and a predetermined amount of interference occurring at $P_5$ and $P_6$ which is less than the amount occurring at $P_3$ and $P_4$. The method of the present invention further comprising the maximum amount of interference comprising 1 to 3 millimeters of interference, preferably 1 to 2 millimeters, the amount of interference at $P_3$ and $P_4$ comprising 1 to 2 millimeters of interference, preferably 1 to 1.5 millimeters, the amount of interference at $P_5$ and $P_6$ comprising ⅜ to 1.5 millimeters of interference, preferably ⅜ to 1 millimeter, the maximum amount of interference comprising 11 to 30 percent interference, preferably 11 to 20 percent, the amount of interference at $P_3$ and $P_4$ comprising 11 to 18.7 percent interference, preferably 11 to 14 percent, and the amount of interference at $P_5$ and $P_6$ comprising 7.5 to 13.8 percent interference, preferably 7.5 to 9.2 percent.

An implant according to the present invention can be forged, machined or cast utilizing any biologically inert material, such as Vitallium ™, titanium, stainless steel, ceramics, polymers or plastics, and may be multi-layer combinations thereof.

Referring to FIG. 1, the hip implant according to the present invention includes a body member or stem 2 which tapers in the proximal to distal direction. As used herein, distal refers to the portion of the prosthesis positioned farthest within the bone canal. Further, the cross-section of the stem 2 preferably changes from circular at the distal end 3 of the stem to substantially greater medial-lateral dimensions as compared with anterior-posterior dimensions at the proximal end 4 of the stem 2. Also, the anterior-posterior width of the stem 2 gradually becomes substantially greater adjacent the lateral side 5 of the implant than the corresponding length adjacent the medial side 6 nearer the proximal end 4 of the stem.

Figure 6:
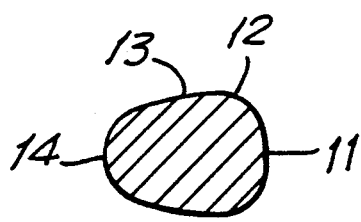
FIG. 6 is a cross-sectional view taken along line B—B of FIG. 1.
Figure 5:
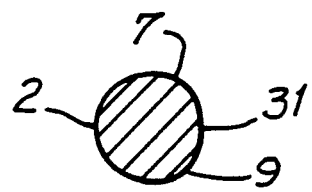
FIG. 5 is a cross-sectional view taken along line C—C of FIG. 1.

In a preferred embodiment of the present invention, the stem 2 has an outside diameter of 0.406 in. at point 30 near distal end 3 of FIG. 1 where the stem is circular in cross-section. As illustrated in FIG. 4, the cross-sectional diameter of stem 2 at line D—D of FIG. 1 is 0.492 in., and the stem is circular in cross-section. As shown in FIG. 5 the cross-sectional view along line C—C of FIG. 1 is not circular. Here the stem 2 has dimensions of 0.597 in. in the medial-lateral direction and 0.579 in. in the anterior-posterior direction. Referring to FIG. 6, at line B—B of FIG. 1 the cross-section of stem 2 has dimensions of 0.913 in. in the medial-lateral direction and 0.672 in. in the anterior-posterior direction. Also the dimensions as shown in FIG. 7 along line A—A of FIG. 1 are preferably 1.5 in. in the medial-lateral direction and 0.832 in. in the anterior-posterior direction on the lateral side.

With reference to the curvature of the radius of the cross-sections of the stem 2, these gradually transform from a circular shape at the distal end 3 to a substantially greater anterior-posterior length on the lateral side than a corresponding length on the medial side.

As used herein the term "radial curvature" will designate a measure of the radius from a corresponding center of the circumference or portion of the cross-section of the stem, and the number given for the radial curvature will correspond to the radius which a circle drawn possessing that degree of curvature would possess. For example, referring to FIG. 6 at point 14 the radial curvature is 0.25 which indicates that if a circle were drawn beginning at point 14 and possessing the same degree of curvature as is shown at point 14, the radius of the circle would be 0.25.

According to a preferred embodiment, FIG. 4 illustrates that the cross-section of the stem 2 is circular at line D—D of FIG. 1 and has the cross-section at line C—C of FIG. 1 possesses a radial curvature of 0.41 at point 31, 0.36 at point 7 and 0.34 at point 8. Since the stem 2 is symmetrical about the medial-lateral axis, thus the radial curvature is also 0.36 at point 9. The symmetry of the stem about the medial-lateral axis continues in the proximal direction up to point 10 on the medial side of line A—A of FIG. 1. FIG. 6 illustrates a cross-section at line B—B of FIG. 1 which has a radial curvature of 1.00 at point 11, 0.22 at point 12, 0.67 at point 13 and 0.25 at point 14. FIG. 7 illustrates a cross-section along line A—A of FIG. 1 preferably a radial curvature of 1.00 at point 15, 0.22 at point 16, 1.25 at point 17 and 0.30 at point 18. Line A—A of FIG. 1 bends 30° towards the distal end 3 of the stem at point 19.

The proximal end 4 of the stem 2 is provided with a neck 20 extending at a 45° angle in the medial direction. The proximal end of the neck 20 is provided with a peg 21 which is designed to receive a joint head as shown in FIG. 1.

The neck 20 preferably is 0.865 in. in length from point 22 on line A—A of FIG. 1 to the distal end of peg 21. The neck 20 has a circular cross-section taken along line F—F of FIG. 1 and preferably has an outside diameter of 0.512 in. Neck 20 narrows toward the proximal end at a slope of 1°25', and is provided with a radial curvature of 0.09 at point 23 where neck 20 meets peg 21.

At its distal end, peg 21 is circular, and has an outside diameter of 0.536 in. Peg 21 narrows toward its proximal end at a slope of 1°25'15" resulting in an outside diameter of 0.506 in. at point 24 with a length of 0.659 in. between the distal end of peg 21 and point 24. At its proximal end, peg 21 is provided with a 0.06 in. by 45° bevel.

Referring to FIG. 9, the implant has a perpendicular length of 2.12 in. from the proximal end of peg 21 to the lateral side of the proximal end of stem 2. Stem 2 is provided with a threaded cavity 25 on the top side of its proximal end, designed to threadedly engage a drive which may be used for insertion or removal of the implant into or out of a bone. Threaded cavity 25 has an inner diameter of 0.25 in. and a depth of 0.30 in. A second cavity 26 may be provided adjacent cavity 25 at its lateral end. Second cavity 26 extends 0.13 in. from the lateral side of cavity 25, and 0.100 in. deep and 0.094 in. wide.

The length of stem 2 can be 5.80 in. on its lateral side from the proximal end to the distal end.

Referring to FIGS. 1-3, the stem 2 is provided with horizontal grooves 27 on its proximal end. The grooves 27 are uniformly spaced vertically and are positioned at the edges, i.e., the stem's antero-lateral, postero-lateral, antero-medial and postero-medial edges.

Referring to FIG. 3, the antero-medial and postero-medial edges of stem 2 are preferably provided with five uniformly vertically spaced horizontal grooves. Each groove is 0.06 in wide and 0.04 in. deep, with center to center spacing of 0.18 in. between each pair of parallel adjacent grooves. A distance of 0.20 in. is maintained between the anterior edges of the postero-medial edge grooves and the posterio edges of the antero-medial edge grooves on the medial side of the stem 2. The horizontal centerline of the grooves is 0.15 in. from the closest portion of the proximal edge of stem 2.

Referring to FIG. 2, the antero-lateral and postero-lateral edges of stem 2 are each preferably provided with four uniformly spaced horizontal grooves. A distance of 0.30 in. is maintained between the anterior edges of the postero-lateral edge grooves and the posterior edges of the antero-lateral edge grooves on the lateral side of the stem.

Referring to FIG. 1, on the anterior and posterior sides the antero-medial and postero-medial edge grooves extend approximately 0.25 in., and the antero-lateral and postero-lateral edge grooves extend approximately 0.317 in.

In the preferred embodiment the distal-most antero-lateral and postero-lateral edge grooves are on the same medial-lateral plane as the proximal-most antero-medial and postero-medial edge grooves.

The above-described grooves are preferably formed by forging the device.

Referring to FIGS. 1 and 15, at least one and preferably both of the anterior and posterior sides of the proximal end of the stem are provided with a substantially randomly patterned array of multiple curved-line surface unevenness, such as indentations or protrusions, defining a random texture ("EDM"). The cancellous texture is preferably formed by forging the device to a depth of 0.020 in.

The macro cancellous texture covers an area of the anterior and posterior sides of the stem defined at its lateral edge by a line beginning distally 1.5 in. from the proximal end of the lateral side of the device, and extending substantially to the proximal end of the stem while maintaining 0.030 in. clearance with the medial edges of the antero-lateral or postero-lateral edge grooves. The proximal and distal sides of the macro cancellous texture extend at 30° angles with the lateral-medial axis in the medial-distal direction. The medial border of the texture maintains a 0.030 in. clearance with the lateral edges of the antero-medial and postero-medial edge grooves.

Before the prosthetic device is implanted, a broach is inserted into the bone canal to form the proximal endosteal envelope by exposing strong cancellous bone in the metaphysis. The broach also indicates the final level of the femoral neck osteotomy and the correct position of the stem.

The broach has a shape which corresponds to the shape of stem 2 of the present invention such that the bone canal may be prepared in a manner which assures that the side or sides of the bone cavity which possess a relatively substantial layer of cancellous bone will form an interference press-fit with a portion of the stem of the prosthesis. The side or sides of the bone cavity which do not possess a relatively substantial layer of cancellous bone but rather possess a layer substantially of cortical bone will not interfere with the stem but will maintain a substantially line-to-line fit with a portion of the stem.

As illustrated in FIG. 14, when the preferred embodiment of the present invention is implanted into a human femur, the proximal end of the stem 2 will maintain an interference press-fit with the lateral side and adjacent portions of the anterior and posterior sides of the bone envelope and a substantially line-to-line fit with the medial side and adjacent portions of the anterior and posterior sides of the bone cavity or envelope. It is preferred that an interference press-fit will be maintained at least along the entire lateral side of the proximal end of the stem, and a line-to-line fit will be maintained at least along the entire medial side of the proximal end of the stem.

Figure 12:
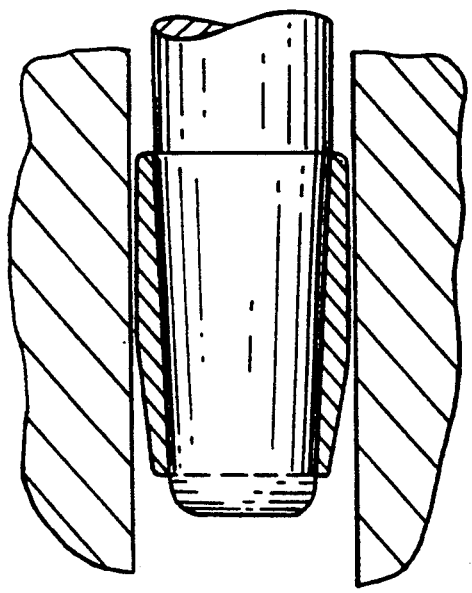
FIG. 12 is a cross-sectional view taken along line 12—12 of FIG. 1 illustrating the distal end of the hip prosthesis of FIG. 1 positioned in a distal sleeve according to the present invention.
Figure 8:
FIG. 8 is a cross-sectional view taken along line F—F of FIG. 1.

The distal end of the stem is provided with a distal sleeve illustrated in FIG. 12, prior to implantation to assure proper alignment of the device within the bone canal.

The distal sleeve 32 is substantially cylindrical and hollow, and provided with an interior conical slope of 4°30′ in the proximal-distal direction such that the distal sleeve can securely engage the distal end of stem 2 when forced thereon. The distal end of the distal sleeve is provided with a 9° taper on a portion of the outside diameter such that the distal sleeve can be more easily inserted into the bone canal. The dimensions of the distal sleeve vary according to the stem size utilized as well as according to the size of the bone canal. Such distal sleeve 32 also aids in controlling micromotion of the stem 2 within the canal as discussed in P. C. Noble et al., "Distal Stem Centralization Affects The Acute Fixation Of Cementless Femoral Stems", copy of which is attached hereto and incorporated herein in its entirety.

The preferred embodiment of the present invention can be implanted according to typical surgical techniques further incorporating methods according to the present invention as disclosed herein. Several aspects of a typical technique embodying the present invention are noted below.

The medullary canal is reamed and the O.D. size of the last flexible reamer used is noted, as this approximates the diameter of the distal sleeve necessary for correct positioning of the tip of the femoral component. The close distal fit restricts implant/bone micromotion and centralizes the distal stem to provide optimal implant stability. Distal sleeves may be provided in OD sizes from 11 to 20 mm, all in 1 mm increments.

Preoperative sizing from templates provides a starting point for selecting the appropriate femoral broach. This instrument forms the proximal endosteal envelope by exposing strong cancellous bone in the metaphysis, and provides for a nonuniform interference, press-fit between the body member and the bone cavity, in accordance with the present invention. It also indicates the final level of the femoral neck osteotomy and the correct position of the femoral component.

Femoral broaches may be provided in a number of sizes corresponding to the dimensions of each implant and to the configurations and dimensions necessary in order to provide a press-fit in accordance with the present invention. Each broach comes with a detachable handle to allow impacting and extracting. The cutting teeth are located in the proximal section only, and this instrument cuts bone only when driven distally into the bone. The broach is driven down the canal with a mallet, keeping it aligned with the femoral axis. After the broach is properly inserted into the bone cavity, and a fit in accordance with the present invention is obtained, the broach is removed from the bone cavity.

Prior to implantation, the appropriate size distal sleeve is placed on the stem and an appropriate stem impactor/extractor is placed in the proximal threaded hole 25. This assembly is placed in an appropriate distal sleeve impactor The stem impactor is tapped with a mallot. The assembly is removed from the sleeve impactor and placed in the prepared femoral canal.

We claim:

1. A method comprising preparing an intramedullary canal of a femur for placement of a bone prosthesis therein, said bone prosthesis having a predetermined shape in its proximal portion, wherein the intramedullary canal is prepared in its proximal portion so that the inner wall of the entire lateral side possesses a substantial surface layer of cancellous bone and provides an interference press-fit with the lateral side of the proximal portion of said bone prosthesis and the inner wall of the entire media side possesses a surface layer substantially comprised of cortical bone and provides a substantially line-to-line fit with the medial side of the proximal portion of said bone prosthesis and a portion of the inner wall of each of the anterior and posterior sides possesses a substantial surface layer of cancellous bone and provides an interference press-fit with the corresponding proximal portion of said bone prosthesis and a portion of the inner wall of each of the anterior and posterior sides possesses a surface layer substantially comprised of cortical bone and provides a substantially line-to-line fit with the corresponding proximal portion of said bone prosthesis.

2. A method according to claim 1 further comprising preparing said entire lateral side of said intramedullary canal so as to provide an interference press-fit with the entire lateral side of said bone prosthesis and preparing said entire medial side of said intramedullary canal so as to provide a substantially line-to-line fit with the entire medial side of said bone prosthesis.

3. A method for implanting a femoral hip prosthesis comprising:
 a) preparing a bone cavity in th proximal portion of a femur by inserting and removing a broach from the proximal femoral intramedullary canal, said broach being sized so as to cause the interior wall of the proximal portion of the bone cavity to be comprised substantially of cortical bone along the medial side and to be comprised substantially of cancellous bone along the lateral side;
 b) inserting a femoral hip prosthesis into the prepared bone cavity, the proximal portion of said femoral hip prosthesis being sized so as to provide a substantially line-to-line fit with the bone cavity along the medial side and an interference fit along the lateral side.

4. A method according to claim 3 wherein said broach is sized so as to cause the interior wall of the proximal portion of the bone cavity to be comprised substantially of cortical bone on the anterior and posterior sides adjacent the medial side and to be comprised substantially of cancellous bone on the anterior and posterior sides adjacent the lateral side, and the proximal portion of said femoral hip prosthesis is sized so as to provide a substantially line-to-line fit along the anterior and posterior sides adjacent the medial side and an interference fit along the anterior and posterior sides adjacent the lateral side.

5. A method for implanting a femoral hip prosthesis comprising:
 a) preparing a bone cavity in the proximal portion of a femur by inserting and removing a broach from the proximal femoral intramedullary canal, the proximal portion of said broach being sized so as to cause the interior wall of the proximal portion of the bone cavity to be comprised substantially of cortical bone along the medial side and substantially cancellous bone along the lateral side; side;
 b) inserting a femoral hip prosthesis into the prepared bone cavity; and
 wherein the proximal portions of said broach and said femoral hip prosthesis are sized relative to each other so as to provide a substantially line-to-line fit between the proximal portion of the femoral hip prosthesis and the medial side of the bone cavity and an interference fit between the proximal portion of the femoral hip prosthesis and the lateral side of the bone cavity.

6. A method according to claim 5 wherein said femoral hip prosthesis comprises a neck and a stem, said stem defining a longitudinal axis and a circumference, said stem having a distal portion and a proximal portion, said proximal portion having an anterior side, a posterior side, a lateral side and a medial side, an antero-medial corner, an antero-lateral corner, a postero-medial corner and a postero-lateral corner, said stem being provided with at least one groove along each of the antero-lateral, postero-lateral, antero-medial and postero-medial corners, each of said grooves extending transverse to said longitudinal axis of said stem and each of said grooves terminating adjacent each said corner.

7. A method according to claim 5 wherein said broach is sized so as to cause the interior wall of the proximal portion of the bone cavity to be comprised substantially of cortical bone along the anterior and posterior sides adjacent the medial side and comprised substantially of cancellous bone along the anterior and posterior sides adjacent the lateral side; and
 wherein the proximal portions of said broach and said femoral hip prosthesis are size relative to each other so as to provide a substantially line-to-line fit between the proximal portion of the femoral hip prosthesis and the anterior and posterior sides of the bone cavity adjacent the medial side and an interference fit between the proximal portion of the femoral hip prosthesis and the anterior and posterior sides of the bone cavity adjacent the lateral side.

* * * * *

UNITED STATES PATENT AND TRADEMARK OFFICE
CERTIFICATE OF CORRECTION

PATENT NO. : 5,062,854

DATED : November 5, 1991

INVENTOR(S) : Noble, et. al.

It is certified that error appears in the above-identified patent and that said Letters Patent is hereby corrected as shown below:

Col. 12, claim 1, line 10, "media" and insert --medial-- therefor.

Col. 13, claim 2, line 4, after "prosthesis" insert --,--.

Col. 13, claim 3, line 3, delete "th" and insert --the-- therefor.

Col. 14, claim 5, line 10, delete "side;".

Col. 14, claim 7, line 9, delete "size" and insert --sized-- therefor.

Signed and Sealed this

Twenty-third Day of March, 1993

Attest:

STEPHEN G. KUNIN

*Attesting Officer*  *Acting Commissioner of Patents and Trademarks*